US008585769B2

(12) United States Patent
Vankoski et al.

(10) Patent No.: US 8,585,769 B2
(45) Date of Patent: Nov. 19, 2013

(54) ACETABULAR LINER SYSTEM (75) Inventors: Stephen J. Vankoski, Fort Wayne, IN (US); Charles D. Persons, Columbia City, IN (US); Tyler Boggs, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 98 days.

(21) Appl. No.: 13/245,169

(22) Filed: Sep. 26, 2011

(65) Prior Publication Data
US 2012/0185059 A1 Jul. 19, 2012

Related U.S. Application Data (60) Provisional application No. 61/432,821, filed on Jan. 14, 2011.

(51) Int. Cl.
*A61F 2/34* (2006.01)
(52) U.S. Cl.
USPC .................. 623/22.24; 623/22.21; 623/22.26
(58) Field of Classification Search
USPC .......... 623/22.21, 22.24, 22.26, 22.28, 22.29, 623/22.19, 22.25, 22.3
See application file for complete search history.

(56) References Cited

U.S. PATENT DOCUMENTS

| 5,725,591 | A | * | 3/1998 | DeCarlo et al. ............ 623/22.29 |
|---|---|---|---|---|
| 5,766,260 | A | | 6/1998 | Whiteside |
| 5,935,175 | A | | 8/1999 | Ostiguy, Jr. et al. |
| 6,152,961 | A | | 11/2000 | Ostiguy, Jr. et al. |
| 6,162,256 | A | * | 12/2000 | Ostiguy et al. ............. 623/22.26 |
| 6,206,929 | B1 | | 3/2001 | Ochoa et al. |
| 6,475,243 | B1 | | 11/2002 | Sheldon et al. |
| 6,610,097 | B2 | | 8/2003 | Serbousek et al. |
| 6,827,742 | B2 | * | 12/2004 | Hayes et al. ............... 623/22.28 |
| RE40,090 | E | | 2/2008 | Whiteside |
| 7,572,294 | B2 | | 8/2009 | Meridew et al. |
| 7,713,306 | B2 | | 5/2010 | Gibbs |
| 7,780,739 | B2 | | 8/2010 | Lakin et al. |
| 7,846,212 | B2 | * | 12/2010 | Lewis et al. ............... 623/22.24 |
| 7,850,738 | B2 | | 12/2010 | Hayes, Jr. et al. |
| 2003/0114934 | A1 | | 6/2003 | Steinberg |

(Continued)

FOREIGN PATENT DOCUMENTS

WO    WO2007/121313 A2    10/2007

OTHER PUBLICATIONS

Yongde Zhang, Peter Ahn, Daniel Fitzpatrick, et al., Interfacial Frictional Behavior: Cancellous Bone, Cortical Bone, and a Novel Porous Tantalum Biomaterial, Journal of Musculoskeletal Research, vol. 3 No. 4, 1999, pp. 245-251.*

(Continued)

*Primary Examiner* — David Isabella
*Assistant Examiner* — Dinah Baria
(74) *Attorney, Agent, or Firm* — Schwegman, Lundberg & Woessner P.A.

(57) ABSTRACT

An acetabular cup assembly for use in the replacement of a hip joint, including a shell having a substantially hemispherical outer surface and an inner surface. The inner surface includes a groove extending at least partially around the inner surface. A provisional liner is provided which is receivable within the shell, the liner including a hemispherical cavity and articulation surface for receipt of the femoral head of a femoral prosthesis, and at least one flexible tab portion which engages the groove of the shell in a snap-fit manner.

20 Claims, 8 Drawing Sheets

(56) References Cited

U.S. PATENT DOCUMENTS

| | | |
|---|---|---|
| 2007/0219640 A1 | 9/2007 | Steinberg |
| 2007/0250175 A1 | 10/2007 | Meridew et al. |
| 2009/0005879 A1 | 1/2009 | Tuke et al. |
| 2010/0161072 A1* | 6/2010 | Drescher .................... 623/22.29 |
| 2011/0015753 A1* | 1/2011 | Meridew .................... 623/22.24 |

OTHER PUBLICATIONS

Zimmer Continuum Acetabular System, Surgical Technique, Zimmer 2011, 32 pages.

Zimmer Continuum Acetabular System, Surgical Technique, Zimmer 2009, 25 pages.

* cited by examiner

FIG_5

ACETABULAR LINER SYSTEM

CROSS-REFERENCE TO RELATED APPLICATIONS

This application claims priority under Title 35, U.S.C. §119(e) to U.S. Provisional Patent Application Ser. No. 61/432,821, filed Jan. 14, 2010, entitled PROVISIONAL LINER SYSTEM, the entire disclosure of which is hereby expressly incorporated by reference herein.

BACKGROUND

1. Field of the Disclosure

The present disclosure relates to orthopaedic implants and, in particular, to acetabular cup assemblies of hip prostheses.

2. Description of the Related Art

Total hip arthroplasty is often used to restore function to a diseased or injured hip joint. Positions and directions relative to the hip joint may be described in terms of proximal being nearer the hip joint, distal being further from the hip joint, anterior being nearer the front of the body, posterior being nearer the back of the body, medial being nearer the centerline of the body, and lateral being further from the center line of the body. In total hip arthroplasty, surfaces of the femur and pelvis are prepared, such as by cutting and/or reaming, and replaced with substitute implants. In a typical case, the implants include a hip stem component, a femoral head component, and an acetabular component.

The acetabular component typically includes a shell having substantially hemispherical outer and inner surfaces. The outer surface is configured for bone ingrowth to anchor the shell in the acetabulum, and the inner surface receives a prosthetic liner formed of a bearing material such as ultra high molecular weight polyethylene (UHWMPE), for example. During the total hip arthroplasty procedure it is often desired to use provisional liners on a trial basis to ascertain the kinematics and/or range of motion of the joint prior to final fitting of the prosthetic liner into the shell. In this procedure, a provisional liner is temporarily secured within the shell, such as via one or more fasteners, and permits a trial reduction of the joint in which the femoral head is received within the provisional liner to assess the kinematics and/or range of motion of the joint. The provisional liner may be removed and replaced with other provisional liners as necessary until the proper size and/or orientation is determined. The provisional liner is then removed and replaced with a prosthetic liner corresponding to the selected provisional liner.

SUMMARY

The present disclosure provides an acetabular cup assembly for use in the replacement of a hip joint, including a shell having a substantially hemispherical outer surface and an inner surface. The inner surface includes a groove extending at least partially around the inner surface. A provisional liner is provided which is receivable within the shell, the liner including a hemispherical cavity and articulation surface for receipt of the femoral head of a femoral prosthesis, and at least one flexible tab portion which engages the groove of the shell in a snap-fit manner. In use, a suitable provisional liner is selected and snap-fittingly inserted into the shell in order to evaluate the kinematics and/or range of motion of the joint, with the snap-fit providing an audible and/or tactile feedback that the liner is fully seated. The provisional liner is easily removed by disengaging the flexible tab portions from the shell groove using a readily-available instrument such as a forceps.

In one form thereof, the present disclosure provides an acetabular cup assembly for use in replacement of a hip joint, the assembly defining perpendicular axial and radial directions, including a shell including an equatorial region, a polar region, an outer surface, and an inner surface, the inner surface including an internal groove extending at least partially around the inner surface; and a provisional liner receivable within the shell, including a hemispherical articulation surface; and at least one flexible tab portion disposed at an outer periphery of the liner, the tab portion including a recess adjacent the outer periphery and extending inwardly in the radial direction, a cavity disposed axially adjacent the recess and extending inwardly in the radial direction beyond the recess, the tab portion further including at least one protrusion receivable within the groove.

In another form thereof, the present disclosure provides an acetabular cup assembly for use in replacement of a hip joint, the assembly defining perpendicular axial and radial directions, the assembly including a shell including an equatorial region, a polar region, an outer surface and an inner surface, the inner surface including an internal groove extending at least partially around the inner surface; and a provisional liner receivable within the shell, including a hemispherical articulation surface; at least one flexible tab portion defined between a pair of reliefs extending inwardly from an outer periphery of the liner and intersecting the articulation surface, the tab portion including at least one protrusion receivable within the groove.

BRIEF DESCRIPTION OF THE DRAWINGS

The above mentioned and other features and objects of this disclosure, and the manner of attaining them, will become more apparent and the disclosure itself will be better understood by reference to the following description of embodiments of the disclosure taken in conjunction with the accompanying drawings, wherein.

Corresponding reference characters indicate corresponding parts throughout the several views. Although the exemplifications set out herein illustrate an embodiment of the disclosure, the embodiment disclosed below is not intended to be exhaustive or to be construed as limiting the scope of the disclosure to the precise form disclosed.

DETAILED DESCRIPTION

Figure 1:
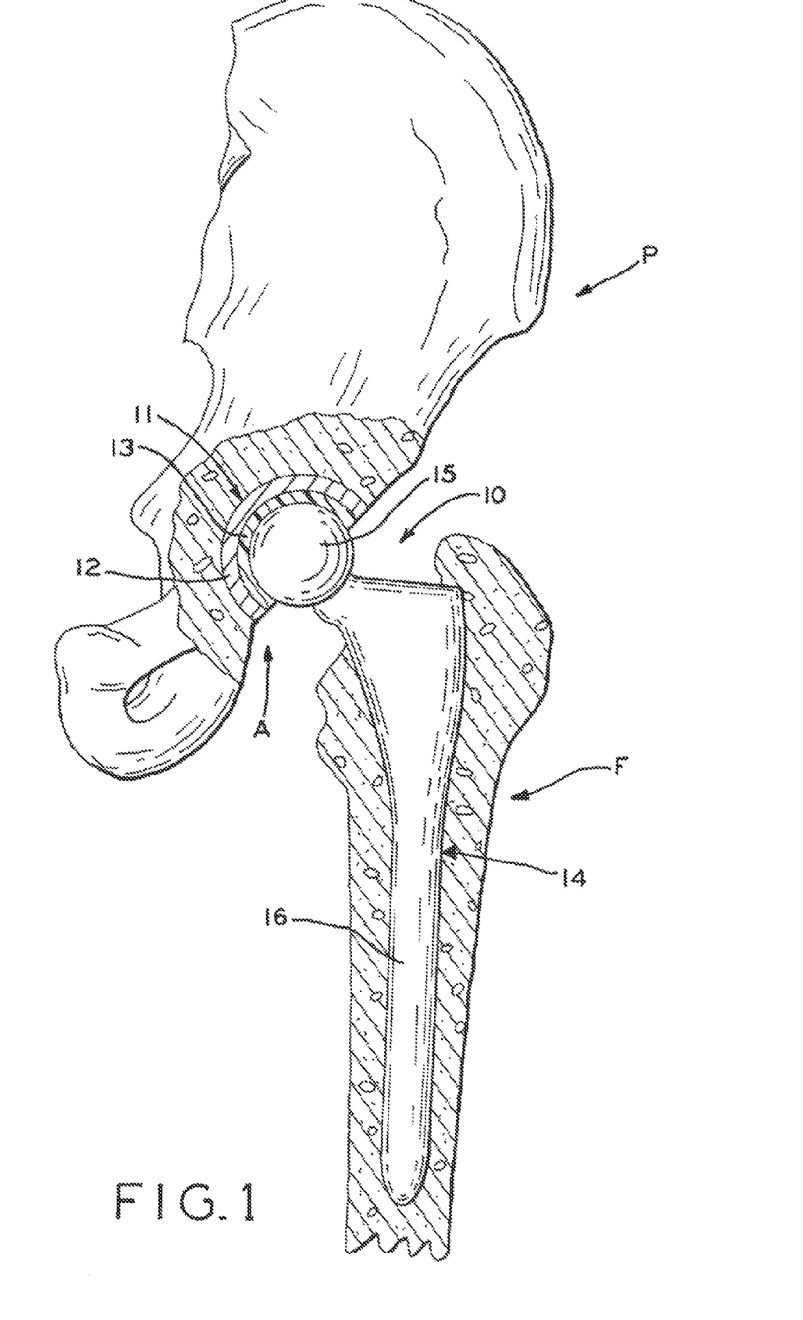
FIG. 1 is a partial sectional view of a hip joint, showing an exemplary prosthetic implant system and the surrounding anatomy.

In FIG. 1, general components associated with an exemplary replacement prosthetic hip implant system 10 are shown in connection with the surrounding anatomy. The prosthetic hip implant system 10 generally includes an acetabular component 11 including a shell 12 and a prosthetic liner 13, and a femoral component 14 including a femoral head 15 and a femoral stem 16. The acetabular component 11 is received within the prepared acetabulum "A" of the pelvis "P", the femoral component 14 is received within the prepared canal of the proximal femur "F", and head 15 of femoral component 14 articulates within liner 13 of acetabular component 11.

Figure 2:
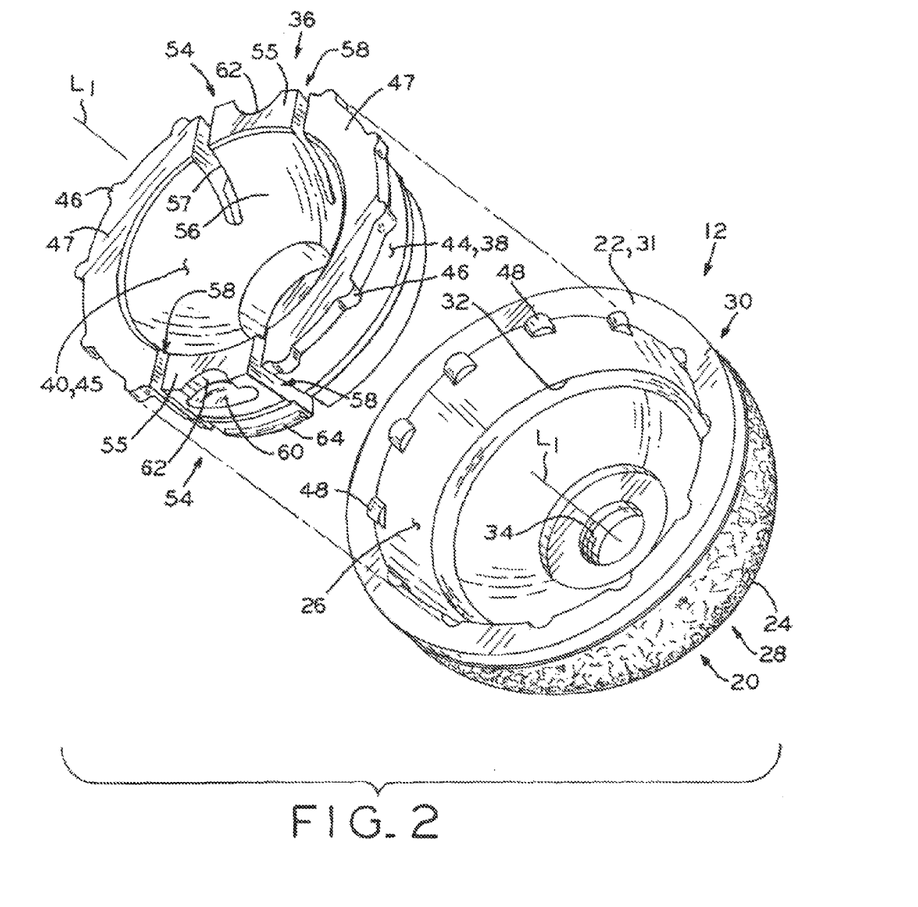
FIG. 2 is an exploded perspective view of an acetabular shell and a provisional liner in accordance with the present disclosure.
Figure 6A:
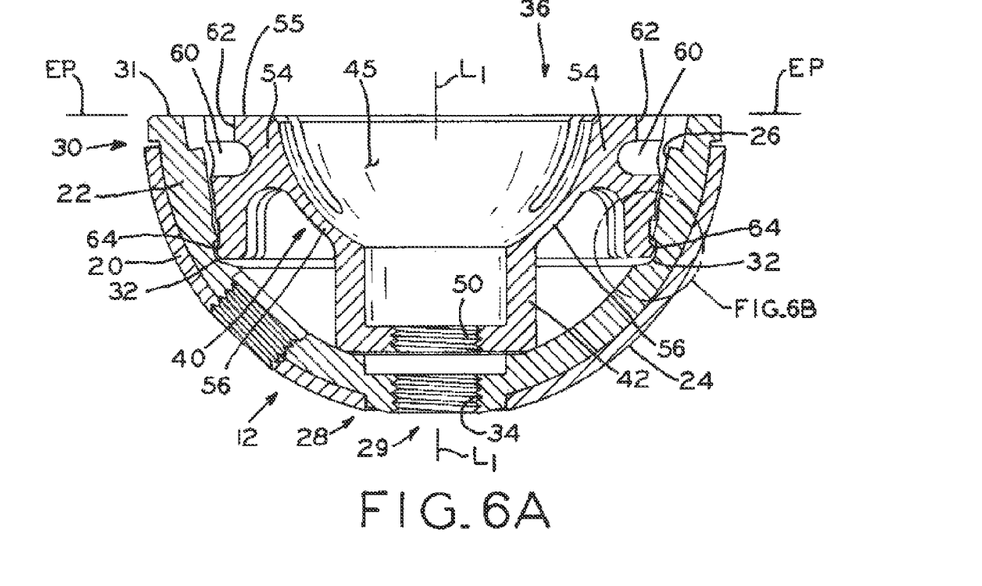
FIG. 6A is a sectional view taken along line 6A-6A of FIG. 5.
Figure 7A:
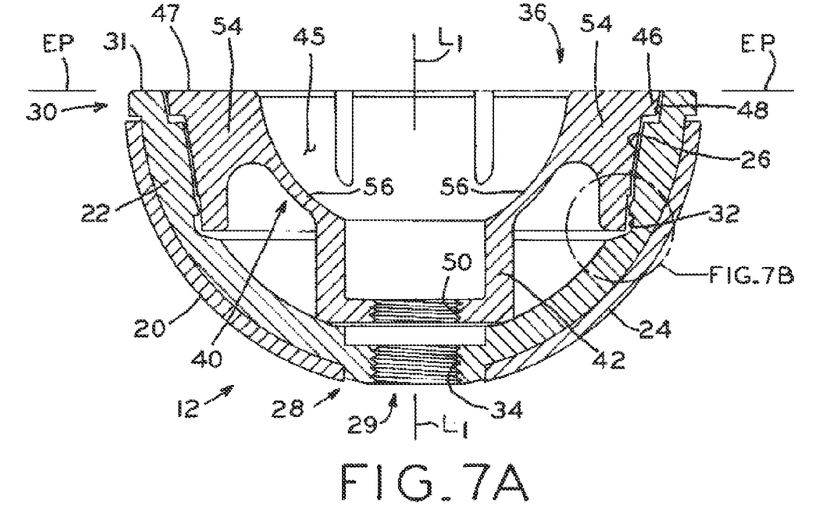
FIG. 7A is a sectional view taken along line 7A-7A of FIG. 5.
Figure 7B:
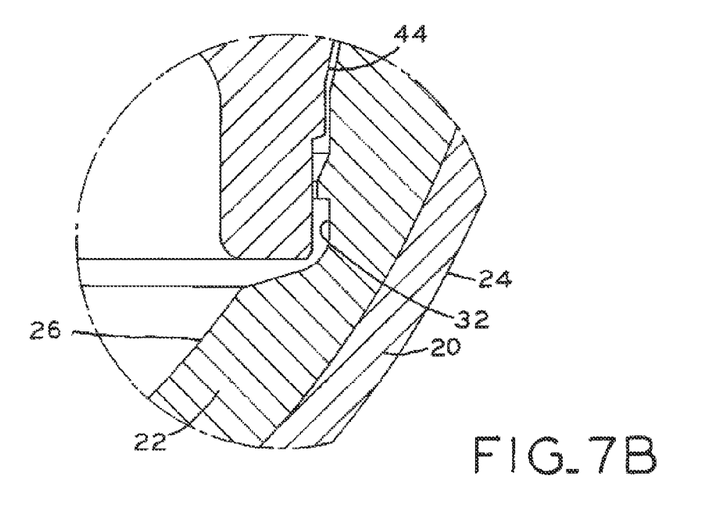
FIG. 7B is a fragmentary view of a portion of FIG. 7A.

Referring to FIGS. 2, 6A and 7A, an exemplary acetabular shell 12 is shown, with which a provisional liner of the present disclosure may be used. However, it should be understood that the present provisional liner may be modified, if necessary, for use with other shells while still retaining the features of the present disclosure, described below. Shell 12 generally includes an outer, bone integration portion or layer 20 and an inner portion or layer 22, with outer portion 20 defining an outer hemispherical surface 24 and inner portion 22 defining an inner surface 26. In the embodiment shown, inner surface 26 of shell 12 is substantially hemispherical, though the shape of inner surface 26 may vary. As best shown in FIGS. 6A and 7A, the overall hemispherical shape of shell 12 generally defines a polar region 28 having a polar end 29 (FIGS. 6A and 7A) and an equatorial region 30 including a planar, annular equatorial surface or ledge 31.

Shell 12 and the provisional liner described below share a common longitudinal axis $L_1$-$L_1$. As used herein, "axial" and "axial direction" refer to longitudinal axis $L_1$-$L_1$ and/or its direction, while "radial" and "radial direction" refer to a direction perpendicular to longitudinal axis $L_1$-$L_1$.

The outer, bone integration portion 20 of shell 12 may be formed of a suitable material which promotes bone ingrowth, such as fiber metal, porous metal, or a porous tantalum having a porosity as low as 55, 65, or 75% and as high as 80, 85, or 90%, for example. An example of a highly porous tantalum material is produced using Trabecular Metal™ Technology generally available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861, the disclosure of which is expressly incorporated herein by reference. In addition to tantalum, other metals such as niobium, or alloys of tantalum and niobium with one another or with other metals may also be used.

Generally, the porous tantalum structure includes a large plurality of ligaments defining open spaces therebetween, with each ligament generally including a carbon core covered by a thin film of metal such as tantalum, for example. The open spaces between the ligaments form a matrix of continuous channels having no dead ends, such that growth of cancellous bone through the porous tantalum structure is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to provide fixation of shell 12 to bone.

The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization.

The inner portion 22 of shell 12 may be made of titanium, titanium alloy, cobalt chromium, cobalt chromium molybdenum, or another suitable metal, metal alloy, or composite biomaterial, for example. Inner surface 26 includes an annular groove 32 which, in the exemplary shell 12 as best shown in FIGS. 6A and 7A, is disposed perpendicular to longitudinal axis $L_1$-$L_1$ and roughly halfway between the polar and equatorial regions 28 and 30 of shell 12, or more specifically, substantially halfway between the equatorial plane EP of the assembly and polar end 29 of shell 12. Shell portions 20 and 22 may include a threaded bore 34 therethrough, disposed centrally within the polar region 28 of shell 12 at polar end 29 and aligned along longitudinal axis $L_1$-$L_1$, for receipt of a fastener (not shown) to secure shell 12 within a prepared acetabulum. Shell 12 may optionally include additional threaded bores in other locations for this purpose.

Figure 3:
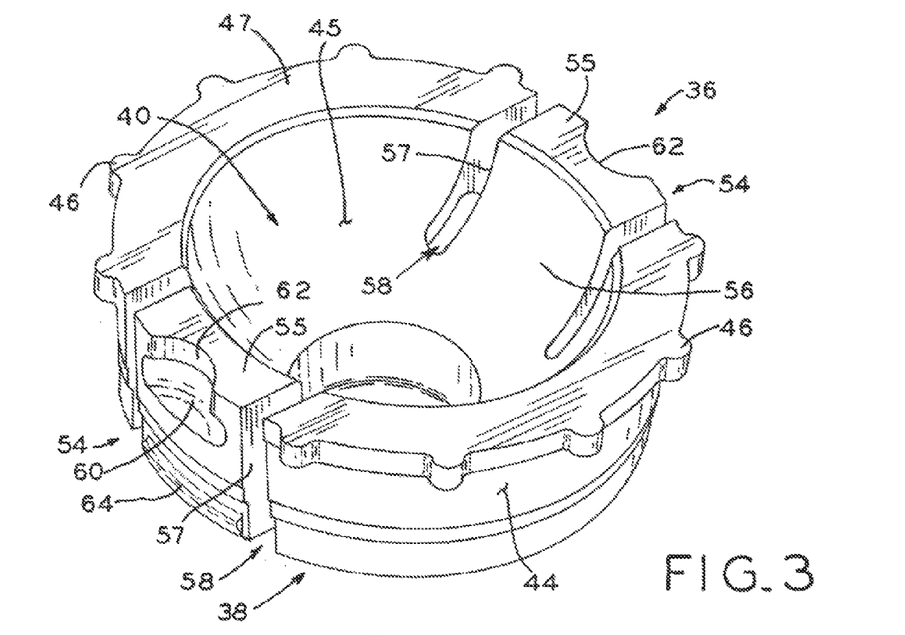
FIG. 3 is an upper perspective view of the provisional liner.
Figure 4:
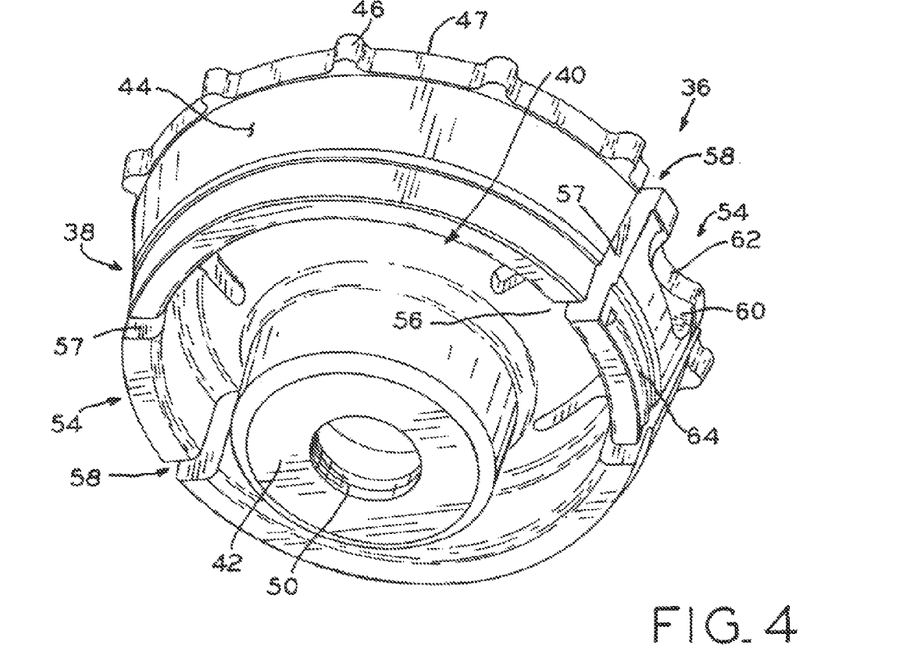
FIG. 4 is a lower perspective view of the provisional liner.

Referring to FIGS. 3 and 4, a provisional liner 36 according to the present disclosure is shown. Provisional liner 36 includes a body having equatorial and polar regions analogous to those of shell 12 within which liner 36 is fitted, together with an outer, annular portion 38 and an inner, substantially hemispherical portion 40 which includes a cylindrical portion 42. Liner 36 may be formed of a suitable plastic material, such as polyphenylsulfone, for example, which is substantially rigid yet allows for flexibility of the flexible tab portions of liner 36, as explained in further detail below. Optionally, provisional liner 36 may be a disposable component intended for a single use.

Figure 5:
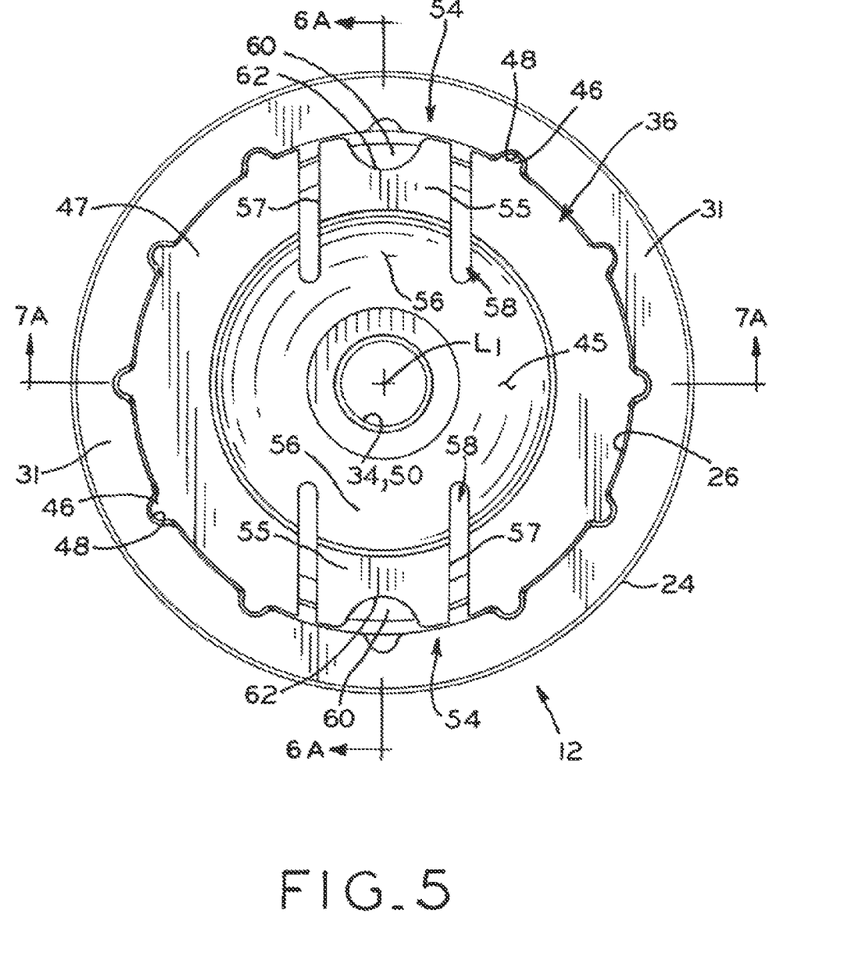
FIG. 5 is a top view of the provisional liner inserted within a shell.
Figures 8A, 8B:
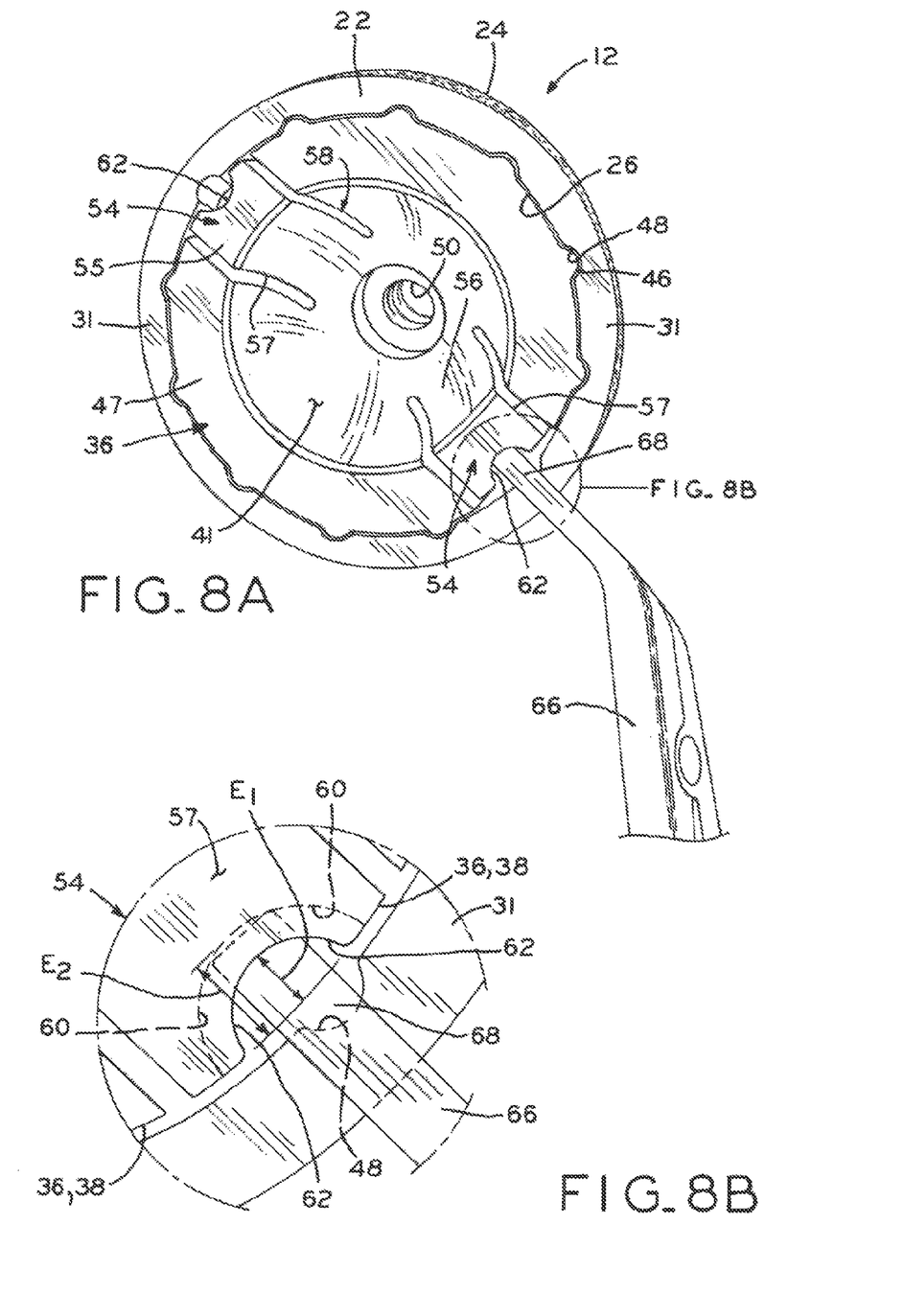
FIG. 8A is a perspective view illustrating an exemplary method of removing the provisional liner from the shell.
FIG. 8B is a fragmentary view of a portion of FIG. 8A.

Outer, annular portion 38 of liner 36 has an outer surface 44 defining a generally frustoconical profile, and optionally includes a series of spaced, radial projections 46 disposed about its outer periphery which, as shown in FIGS. 2, 5, and 8, project from semi-annular flange portions 47 of liner 36 and are receivable within a corresponding series of spaced, radiused recesses 48 disposed about the outer periphery of the equatorial region 30 of shell 12 to prevent relative rotation between liner 36 and shell 12 when liner 36 is received and seated within shell 12 in the manner described below. As best shown in FIGS. 6A and 7A, semi-annular flange portions 47 of liner 36 are substantially coplanar with equatorial surface or ledge 31 of shell 12, with the foregoing each disposed within equatorial plane EP of the shell and liner assembly.

Inner, hemispherical portion 40 of liner 36 has a smooth, hemispherical concave articulation surface 45 adapted to receive the femoral head 15 of a femoral stem component 14 during a trial reduction of a prosthetic hip joint during use of the provisional liner 36. Cylindrical portion 42 extends from the lower region of the inner hemispherical portion 40 and includes a bore 50 alignable with bore 34 of shell 12. Bore 50 may optionally be internally threaded.

Figure 9:
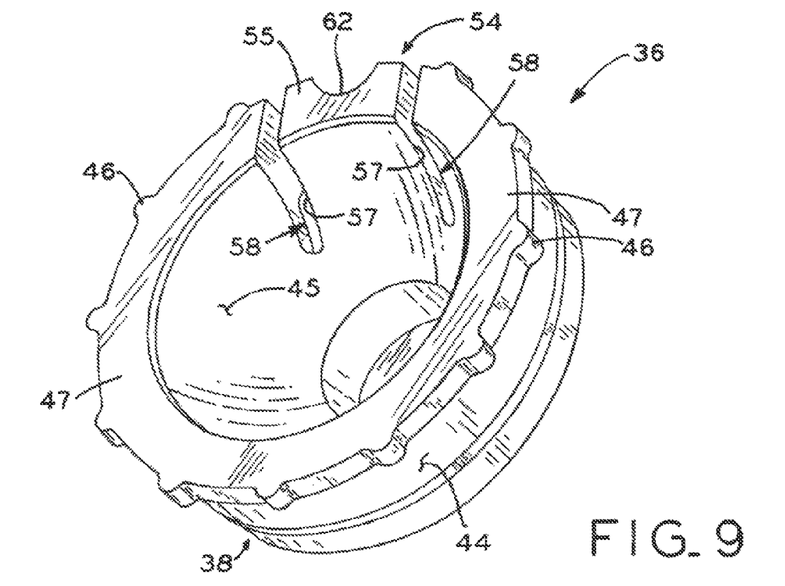
FIG. 9 is a perspective view of a provisional liner in accordance with another embodiment of the present disclosure.

A pair of flexible tab portions 54 are formed in liner 36 for engaging annular groove 32 of shell 12 when liner 36 is received within shell 12 during a surgical procedure, as described below. In the exemplary embodiment, flexible tab portions 54 are shown as two in number, and are positioned on opposite sides of liner 36, i.e., are disposed 180° with respect to one another, and aligned perpendicular to longitudinal axis $L_1$-$L_1$. However, the number and relative spacing of tab portions 54 may vary as desired, and other configurations are possible. In particular, liner 36 may optionally include only a single tab portion 54, as shown in FIG. 9. As also described below, in embodiments where liner 36 includes a pair of tab portions 54 positioned opposite one another, or a single tab portion 54, the actuation of tab portions 54 and disengagement of liner 36 from shell 12 is facilitated.

Each tab portion 54 includes a base portion 56 which, as best seen in FIGS. 6A and 7A, is relatively thin and is integrally or monolithically formed with hemispherical portion 40 of liner 36. The relatively thin profile of base portion 56 allows tab portions 54 to flex slightly with respect to the body portion 38 and 40 of liner 36. Tab portions 54 also have opposing side surfaces 57 with a shape or profile respectively defined by a pair of reliefs or cutouts 58 formed in liner 36, which generally extend parallel to one another from the outer periphery of annular portion 38 of liner 36 and into hemispherical portion 40 of liner 36. As shown, reliefs 58 also may intersect the hemispherical articulation surface 45 of liner 36 such that articulation surface 45 is not hemispherically continuous but is rather interrupted by reliefs 58. The interruption of hemispherical articulation surface 45 by reliefs 58 permit reliefs 58 to be dimensioned relatively large, such that tab portions 54 are easily flexed as described below. Additionally, the interruption of articulation surface 45 by reliefs 58 does not present any potential for structural or wear concerns during a trial reduction, due to the temporary or transitory nature of the trial reduction in a surgical procedure.

Tab portions 54 further include profiled cavities 60 which open to the outer periphery of outer annular portion 38 of liner 36, together with hemispherical recesses 62 which provide access to cavities 60 through the equatorial surfaces 55 of tab portions 54 of liner 36, which are disposed in equatorial plane EP. As best shown in FIG. 8B, recesses 62 extend inwardly form the outer periphery of liner 36 to a first extent $E_1$, while cavities 60 extend inwardly form the outer periphery of liner 36 to a second extent $E_2$ which is greater than the first extent $E_1$. In this manner, cavities 60 are undercut with respect to recesses 62 and the equatorial surfaces 55 of tab portions 54.

Figure 6B:
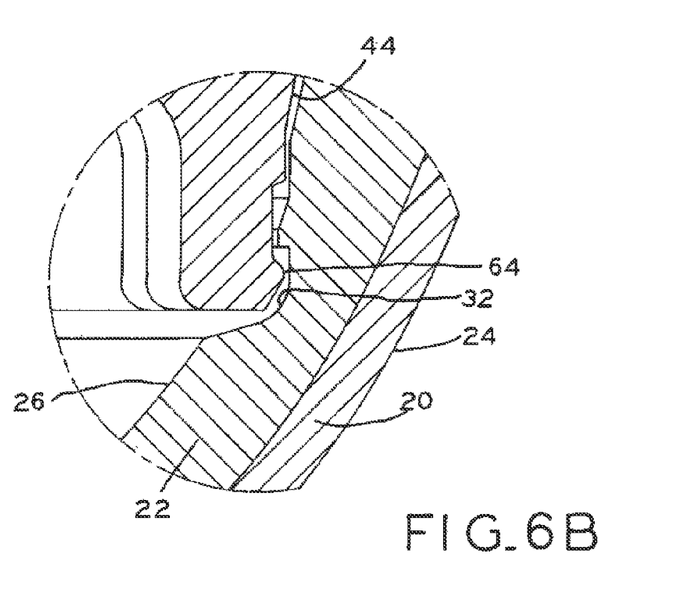
FIG. 6B is a fragmentary view of a portion of FIG. 6A.

A pair of projections 64 are spaced from cavities 60 in the axial direction toward the polar region of liner 36, and project a slight distance in the radial direction from the outer periphery of outer annular portion 38 of liner 36. The ends of projections 64 are somewhat lobe-shaped and are radiused, as most clearly shown in FIG. 6B, to facilitate engagement with, and disengagement from, groove 32.

During a surgical procedure, the acetabulum is prepared in a known manner, such as by reaming, and shell 12 is seated within the prepared acetabulum. Shell 12 is selected from a plurality of shells having different outer diameters, such as ranging from 48 mm and 62 mm, for example. If a trial reduction of the joint is desired, a suitable provisional liner 36 is selected and fitted within shell 12. A plurality of provisional liners 36 may be provided corresponding to the various sizes of shells 12, typically in a plurality of sets having common outer diameters sized to fit within the various shells 12, with each set in turn having a plurality of provisional liners with varying inner diameters, such as ranging from 28 mm and 40 mm, for example. In one embodiment, the plastic material of the liners 36 may be colored differently between each set to provide color coding indicia as to the size of the outer diameters of the provisional liners.

Once a provisional liner 36 has been selected, the liner 36 is inserted within shell 12 as shown in FIGS. 2 and 5-8. In particular, to insert liner 36 within shell 12, the surgeon may place his or her thumbs on flanges 47 and/or tab portions 54 of liner 36 to push liner 36 into shell 12. Projections 64 of tab portions 54 may initially engage interior hemispherical surface 26 of shell 12 proximate annular groove 32 to bias projections 64 and tab portions 54 slightly inwardly, followed by projections 64 and tab portions 54 being return-biased outwardly upon receipt of projections 64 into annular groove 32 when liner 36 is fully seated.

This snap-fit receipt of projections 64 within annular groove 32 may produce an audible "click" sound and/or a tactile response to the surgeon's thumbs, indicating that liner 36 has been fully seated within shell 12. When liner 36 is fully seated, projections 46 around the outer periphery of outer annular portion 38 of liner 36 are received within the corresponding recesses 48 of shell 12 to prevent relative rotation between liner 36 and shell 12. Referring to FIGS. 6A and 7A, the bottom end of cylindrical portion 42 of liner 36 may also be dimensioned to engage the inner surface 26 of shell 12 at the polar region 28 of shell 12. In an optional step, if liner 36 is provided with bore 50, a threaded fastener (not shown) may be inserted through the aligned bores 50 and 34 of liner 36 and shell 12, respectively, and threaded within bore 34 of shell 12 to more securely fix liner 36 to shell 12.

Advantageously, the flexible tab portions 54 of provisional liner 36 facilitate an easy, snap-fit engagement with annular groove 32 of shell 12 to provide an easily perceivable, audible and/or tactile feedback to the surgeon when provisional liner 36 is properly seated within shell 12 and, as described below, to facilitate the easy removal of provisional liner 36 from shell 12 for replacement by either another provisional liner or the final prosthetic liner. The reliefs 58 on either side of tab portions 54 are dimensioned to provide a controlled, yet limited flexibility of tab portions 54, and projections 64 of tab portions 54 are dimensioned to engage annular groove 32 of shell 12 to an extent such that liner 36 is positively secured within shell 12 during a trial reduction procedure, described below, yet tab portions 54 are able to easily flex in a controlled and limited manner when engaged by an instrument for easy removal of liner 36 from shell 12.

Referring generally to FIG. 1, once the selected provisional liner 36 is fitted within shell 12 as described above, the surgeon may perform a trial reduction of the joint in which femoral head 15 of the femoral component 14 is received in an articulating manner against the hemispherical concave articulation surface 45 of liner 36. The surgeon may then assess the joint kinematics and/or range of motion of the joint, and thereafter, may remove and replace liner 36 with another selected liner, followed by re-trialing the joint as necessary until the desired result is achieved.

Once a provisional liner 36 is selected, fitted, and trialed, the liner 36 is removed by use of a suitable instrument 66, as shown in FIGS. 8A and 8B. Advantageously, instrument 66 may be any type of readily available instrument in an operating room, such as a forceps or the end portion of a rongeur or pair surgical scissors, for example. In this manner, a specialized instrument is not needed to remove liner 36. In particular, as shown in FIGS. 8A and 8B, a suitable end portion 68 of instrument 66 is inserted through recess 62 and into the undercut cavity 60 of one of the tab portions 54 to flex the tab portion 54 slightly radially inwardly toward the longitudinal axis $L_1$-$L_1$ of liner 36 to disengage projection 64 of the tab portion 54 from angular groove 32 of shell 12.

As best shown in FIG. 8B, the undercut cavity 60 adjacent recess 62 also provides a lifting surface for lifting an edge of liner 36 along the axial direction of longitudinal axis $L_1$-$L_1$ of liner 36 after disengagement of protrusion 64 of tab portion 54 from annular groove 32 of shell 12 in order to in turn disengage liner 36 from shell 12. In this manner, liner 36 may be released from shell 12 by exerting a slight axial force against the underside of recess 62 to tilt liner 36 slightly with respect to longitudinal axis $L_1$-$L_1$ and thereby release the projection 64 of the opposite tab portion 54 from annular groove 32 of shell 12. In some embodiments, including the embodiment described above in which liner 36 includes a pair of tab portions 54 disposed opposite one another, once a single tab portion 54 released, the lifting of that tab portion 54 on one side of liner 36 tilts liner 36 and at least partially disengages projection 64 of the tab portion 54 on the opposite side of the liner 36 from annular groove 32. In other embodiments, it may be necessary to use a pair of instruments, or perhaps a forceps or scissor-type instrument (not shown) to simultaneously actuate both tab portions 54 in the foregoing manner to release liner 36 from shell 12. In the embodiment of FIG. 9, a liner 36 may have only a single tab portion 54, which may be flexed to release liner 36 for disengagement from shell 12.

Once the provisional liner 36 is removed, a final prosthetic liner 13 (FIG. 1) corresponding in size to the selected provisional liner 36 may be inserted within shell 12, followed by reduction of the joint and completion of the surgical procedure.

Figure 10:
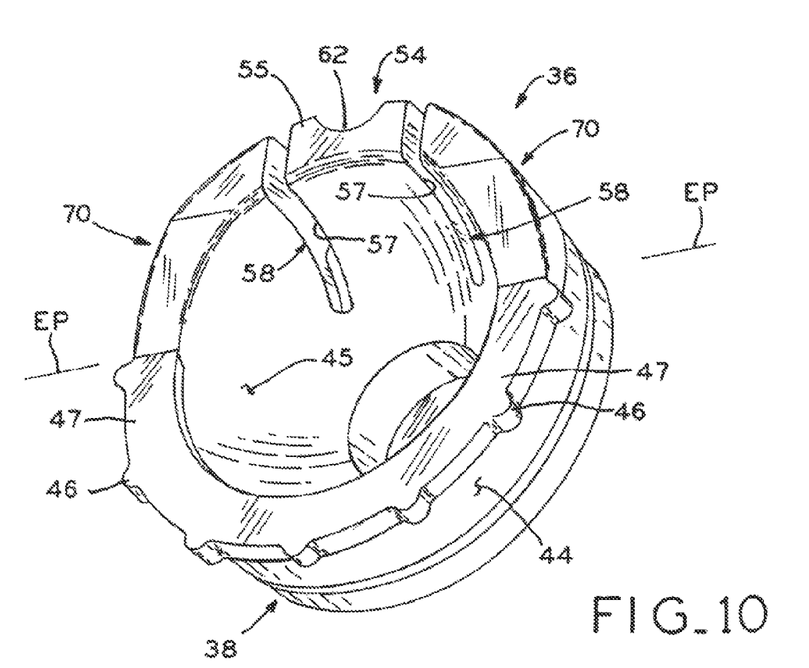
FIG. 10 is a perspective view of a provisional liner in accordance with a further embodiment of the present disclosure.

Referring to FIG. 10, in a further embodiment, liner 36 may include an elevated portion 70 along at least a portion of its outer periphery, which extends from the equatorial plane EP of liner 36 in which flange portions 47 of liner 36 are disposed. Elevated portion 70 generally extends from the outer periphery of liner 36 in an axial direction from equatorial plane EP, and may include a tab portion 54 substantially identical to those described above, which is defined by a pair of reliefs 58. Tab portion 54 functions in the same manner as in the embodiments described above, except that due to the fact that elevated portion 70 is elevated with respect to the equatorial plane EP of liner 36 and shell 12, tab portion 54 may be easily actuated by a surgeon's thumb or finger without need for the use of an instrument to release and disengage liner 36 from shell 12.

While this disclosure has been described as having an exemplary design, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. An acetabular cup assembly for use in replacement of a hip joint, said assembly defining perpendicular axial and radial directions, comprising:
a shell including an equatorial region, a polar region, an outer surface, and an inner surface, said inner surface including an internal groove extending at least partially around said inner surface; and
a liner receivable within said shell, comprising:
a hemispherical articulation surface; and
at least one flexible tab portion disposed at an outer periphery of said liner, said tab portion including a recess opening to said outer periphery and extending inwardly in the radial direction, a cavity in communication with said recess, said cavity disposed axially adjacent said recess and extending inwardly beyond said recess in the radial direction to form an undercut with respect to said recess, and at least one protrusion receivable within said groove.

2. The assembly of claim 1, wherein said recess and said cavity are configured to receive and engage a member or a feature of a surgical instrument.

3. The assembly of claim 1, wherein said at least one flexible tab portion includes a pair of said flexible tab portions disposed opposite one another.

4. The assembly of claim 1, wherein said at least one flexible tab portion comprises a single flexible tab portion.

5. The assembly of claim 1, wherein said tab portion includes a base portion integrally formed with said liner, and a profile at least partially defined by a relief formed in said liner.

6. The assembly of claim 5, wherein said profile of said tab portion is defined between a pair of said reliefs extending inwardly from said outer periphery of said liner, said pair of reliefs intersecting said articulation surface.

7. The assembly of claim 1, wherein said liner includes an elevated portion extending in the axial direction from said outer periphery, said at least one tab portion formed in said elevated portion.

8. The assembly of claim 1, wherein said liner includes a plurality of projections spaced about said outer periphery, said projections receivable within respective recesses in said shell when said liner is received within said shell.

9. The assembly of claim 1, wherein said shell includes a threaded shell bore in said polar region, and said liner includes a liner bore, said liner bore alignable with said shell bore when said liner is received within said shell.

10. The assembly of claim 1, wherein said outer surface of said shell is formed of a porous tantalum material.

11. An acetabular cup assembly for use in replacement of a hip joint, said assembly defining perpendicular axial and radial directions, said assembly comprising:
a shell including an equatorial region, a polar region, an outer surface and an inner surface, said inner surface including an internal groove extending at least partially around said inner surface; and
a liner receivable within said shell, comprising:
a hemispherical articulation surface; and
at least one flexible tab portion defined between a pair of reliefs extending inwardly from an outer periphery of said liner and intersecting said articulation surface, said at least one flexible tab portion including:
at least one protrusion receivable within said groove;
a recess opening to said outer periphery and extending inwardly in the radial direction; and
a cavity in communication with said recess, said cavity disposed axially adjacent said recess and extending inwardly beyond said recess in the radial direction to form an undercut with respect to said recess.

12. The assembly of claim 11, wherein said at least one flexible tab portion comprises a pair of said flexible tab portions disposed opposite one another.

13. The assembly of claim 11, wherein said at least one flexible tab portion comprises only a single flexible tab portion.

14. The assembly of claim 11, wherein said liner includes an elevated portion extending in the axial direction from said outer periphery, said at least one tab portion formed in said elevated portion.

15. The assembly of claim 11, wherein said liner includes a plurality of projections spaced about said outer periphery, said projections receivable within respective recesses in said shell when said liner is received within said shell.

16. The assembly of claim 11, wherein said recess is disposed adjacent a corresponding recess in said shell when said liner is received within said shell.

17. The assembly of claim 11, wherein said outer surface of said shell is formed of a porous tantalum material.

18. The assembly of claim 11, wherein said groove is annular, extends completely around said inner surface, and is disposed approximately half-way between an equatorial plane and a polar plane of said shell.

19. The assembly of claim 16, wherein said liner recess and cavity and said shell recess are configured to cooperatively receive and engage a member or a feature of a surgical instrument when said liner is received within said shell.

20. The assembly of claim 11, wherein said shell includes a threaded shell bore in said polar region, and said liner includes a liner bore, said liner bore alignable with said shell bore when said liner is received within said shell.

* * * * *